United States Patent
Crooks et al.

(10) Patent No.: US 7,312,242 B2
(45) Date of Patent: Dec. 25, 2007

(54) USE OF PARTHENOLIDE DERIVATIVES AS ANTILEUKEMIC AND CYTOTOXIC AGENTS

(75) Inventors: Peter A. Crooks, Nicholasville, KY (US); Craig T. Jordan, Rochester, NY (US); Xiaochen Wei, Lexington, KY (US)

(73) Assignee: University of Kentucky, Lexington, KY (US)

( * ) Notice: Subject to any disclaimer, the term of this patent is extended or adjusted under 35 U.S.C. 154(b) by 171 days.

(21) Appl. No.: 10/888,274

(22) Filed: Jul. 9, 2004

(65) Prior Publication Data
US 2005/0032886 A1 Feb. 10, 2005

Related U.S. Application Data

(60) Provisional application No. 60/486,171, filed on Jul. 11, 2003.

(51) Int. Cl.
*A61K 31/35* (2006.01)

(52) U.S. Cl. ............ 514/456; 514/321; 514/232.8; 514/254.11; 549/299; 548/526; 544/153; 544/378

(58) Field of Classification Search ........... 549/299; 546/197; 548/526; 544/153, 378; 514/468, 514/422, 321, 232.8, 254.11, 456
See application file for complete search history.

(56) References Cited

U.S. PATENT DOCUMENTS

2003/0125373 A1 7/2003 Nakshatri et al. ........... 514/449
2004/0229936 A1 11/2004 Hsieh et al.

OTHER PUBLICATIONS

Ruangrungsi, N et al 'Studies on Thai medicianal plants Ix. Constituents of *Michelia rajaniana*. Two new germacranolide amides' CA 110:151284 (1989).*
See Ross, JJ et al, Low concentration of the feverfew component parthenolide inibit in vitro growth of tumor lines in a cytostatic fashion, PMID: 10193202 (1999).*

Wen, J et al, Oxidative Stress-mediated Apoptosis, The Anticancer Effect of the Sesquiterpene Lactone Parthenolide, J. Biological Chem, 277(41), pp. 38954-38964 (2002).*
Abduazimov, BK et al, Modification of the Sesquiterpane Lactone Arteannuin B and Antimicrobial Activities of the Products Obtained, Chemistry of Natural Compounds, 33(5), (1997) 554-557.*
Cory and Cory, "Lactacystin, a proteasome inhibitor, potentiates the apoptotic effect of parthenolide, an inhibitor of NFkappaB activation, on drug-resistant mouse leukemia L1210 cells" *Anticancer Research* 2002, 22, 3805-9.
Cory and Cory, "Augmentation of apoptosis responses in p53-deficient L1210 cells by compounds directed at blocking NFkappaB activation" *Anticancer Research*, 2001, 21, 3807-11.
Gelfanov et al., "Transformation of interleukin-3-dependent cells without participation of Stat5/bcl-xL: cooperation of akt with aft/erk leads to p65 nuclear factor κB-mediated antiapoptosis involving c-IAP2" *Blood*, 2000, 98, 2508-17.
Kang et al., "Enhancement of 1α,25-dihydroxyvitamin $D_3$-induced differentiation of human leukaemia HL-60 cells into monocytes by parthenolide via inhibition of NF-κB activity" *Brit. J. Pharmacol.* 2002, 135, 1235-44.
Song et al., "A new sesquiterpene lactone from Tsoongiodendron odorum chun" *J. Asian. Nat. Prod. Res.* 2001, 3, 285-91.
Wen et al., "Oxidative stress-mediated apoptosis" *J. Biol. Chem.* 2002, 277, 38954-38964.
U.S. Appl. No. 60/459,769, filed Apr. 02, 2003, Hsieh et al.
Hwang et al., "Synthesis and anti-viral activity of series of sesquiterpene lactones and analogues in the subgenomic HCV replicon system" *Bioorganic and Medicinal Chemistry*14: 83-91 (2006).

* cited by examiner

*Primary Examiner*—Amelia A. Owens
(74) *Attorney, Agent, or Firm*—Greenberg Traurig, LLP

(57) ABSTRACT

Compounds of the formula having anti-tumor activity, wherein $R_1$ and $R_2$ are as described herein 15 Claims, 3 Drawing Sheets

USE OF PARTHENOLIDE DERIVATIVES AS ANTILEUKEMIC AND CYTOTOXIC AGENTS

This application claims priority to provisional application 60/486,171 filed Jul. 11, 2003.

FIELD OF INVENTION

The present invention relates to methods for the structural modification of the sesquiterpene lactone, parthenolide, and the use of these parthenolide derivatives in the treatment of carcinoma. More specifically, the invention relates to the methods to prepare structural analogs of the parent compound, parthenolide, in order to obtain new, pharmacologically active chemical entities with improved water solubility characteristics, and to use them in the treatment of leukemias and other parental and multi-drug resistant human cancers.

BACKGROUND OF THE INVENTION

Sesquiterpene lactones are a group of secondary plant metabolites consisting of a 15-carbon structure containing an α-methylene-γ-butyrolactone moiety and other additional functional group(s). Over the last two to three decades, these terpenoids have received considerable attention due to the broad spectrum of their biological activities, to the plants which produce them, and most importantly, because of their pharmacological effects in humans. About 4,000 of these terpenoids have been isolated and identified, most of them in Asteraceae (Compositae, sunflower family) (Schmidt, *Curr. Org. Chem.* 1999, 3, 577–608). Some of these plants have been used for centuries in indigenous medical practices in different cultures worldwide.

Parthenolide (1) is a Germacrane sesquiterpene lactone with a unique structure. It has been isolated from several different species in Asteraceae (Compositae) family. The well-known Feverfew (*Tanacetum parthenium*) is one of them.

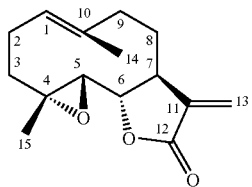

1

Feverfew has been used to reduce fever and pain and in the treatment of migraine and rheumatoid arthritis (Heptinstall et al., ACS Symposium Series (1998), 691 (Phytomedicines of Europe), 158–175.). The active component is parthenolide (1). Recently, it has been revealed that parthenolide (1) can induce tumor apoptosis by the inhibition of NF-κB activities (Cory et al., *Anticancer Research* 2002, 22, 3805–9; Cory et al., *Anticancer Research* 2001, 21, 3807–11; Gelfanov et al., *Blood*, 2000, 98, 2508–17; Kang et al, *Brit. J. Pharmacol.* 2002, 135, 1235–44; Song et al., *J. Asian. Nat. Prod. Res.* 2001, 3, 285–91).

Parthenolide (1) is a lipophilic, neutral lactone with low polarity, and has a low water-solubility. This limits its further development as a therapeutic agent. According to the literature, the α-methylene-γ-butyrolactone moiety in parthenolide (1) appears to be the most important functionality for its anticancer activity (Wen et al, *J. Biol. Chem.* 2002, 277, 38954–38964) and modification of this part of the molecule may cause loss of biological activity. Unfortunately, derivatives obtained from the modification of parthenolide (1 molecule at the 14-methyl group and at the 1,10-carbon-carbon double bond result in loss of antileukemic activity.

SUMMARY OF THE INVENTION

In accordance with the present invention, a novel class of nitrogen-containing parthenolide derivatives with antileukemic activity is presented.

The compounds of the invention are capable of killing leukemia cells. Therapeutic indications include leukemia and all human parental and/or multi-drug resistant cancers; compounds for treating migraine and compounds for the treatment of inflammation.

The invention also provides a pharmaceutical composition comprising an effective amount of a parthenolide derivative compound, or a pharmaceutically acceptable salt thereof, in combination with a pharmaceutically acceptable diluent or carrier.

The invention also provides a method of inhibiting cancer cell growth and metastasis of cancer cells, comprising administering to a mammal afflicted with cancer, an amount of a parthenolide derivative compound, effective to inhibit the growth of said cancer cells.

The invention also provides a method comprising inhibiting cancer cell growth by contacting said cancer cell in vitro or in vivo with an amount of a parthenolide derivative compound, effective to inhibit the growth of said cancer cell.

The invention also provides a parthenolide derivative compound for use in medical therapy (preferably for use in treating cancer, e.g. solid tumors), as well as the use of a parthenolide derivative compound for the manufacture of a medicament useful for the treatment of cancer, e.g. solid tumors.

The invention further provides methods of treating inflammatory diseases and disorders, including, for example, rheumatoid arthritis, osteoarthritis, allergies (such as asthma), and other inflammatory conditions, such as pain, swelling, fever, psoriasis, inflammatory bowel disease, gastrointestinal ulcers, cardiovascular conditions, including ischemic heart disease and atherosclerosis, partial brain damage caused by stroke, skin conditions (eczema, sunburn, acne), leukotriene-mediated inflammatory diseases of lungs, kidneys, gastrointestinal tract, skin, prostatitis, and paradontosis.

The invention further provides methods of treating immune response disorders, whereby the immune response is inappropriate, excessive or lacking. Such disorders include allergic responses, transplant rejection, blood transfusion reaction, and autoimmune disorders such as systemic lupus erythematosus and rheumatoid arthritis.

DETAILED DESCRIPTION OF THE INVENTION

Figure 1:
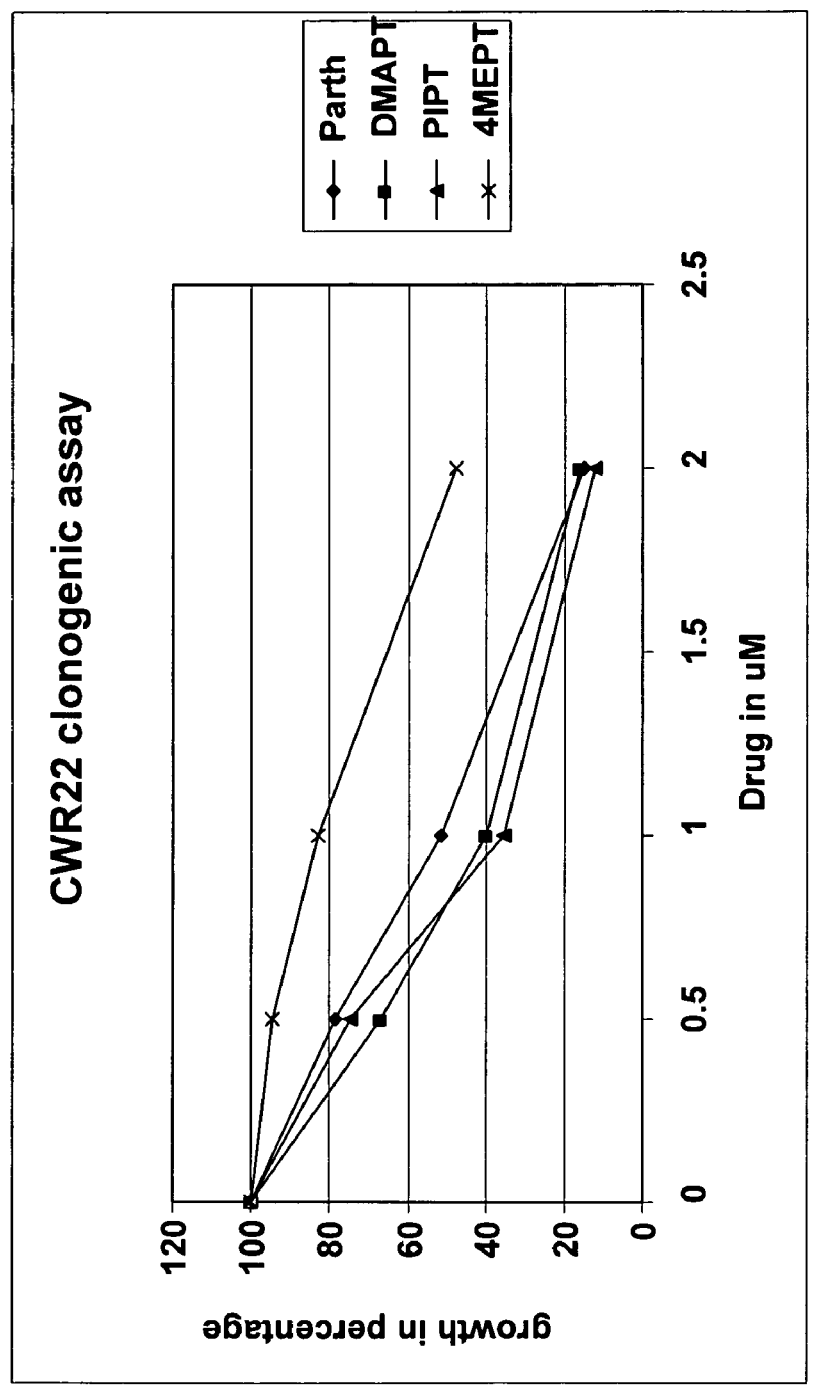
FIG. 1 shows the effectiveness of parthenolide and derivatives of the present invention in the clonogenic assay against prostate cancer cell line CWR22Rv1s.

As used herein, "alkyl" refers to straight or branched chain alkyl groups having in the range of about 1 up to 20 carbon atoms; "substituted alkyl" refers to alkyl groups further bearing one or more substituents such as hydroxy, alkoxy, mercapto, aryl, heterocyclic, halogen, trifluoromethyl, cyano, nitro, amino, carboxyl, carbamate, sulfonyl, sulfonamide and the like; "lower alkyl" means 1 to 8 carbons;

"cycloalkyl" refers to cyclic ring-containing groups containing in the range of about 3 up to 8 carbon atoms, and "substituted cycloalkyl" refers cycloalkyl groups further bearing one or more substituents as set forth above;

"alkenyl" refers to straight or branched chain hydrocarbon groups having at least one carbon-carbon double bond, and having in the range of about 2 up to 20 carbon atoms, and "substituted alkenyl" refers to alkenyl groups further bearing one or more substituents as set forth above;

"alkynyl" refers to straight or branched chain hydrocarbon groups having at least one carbon-carbon triple bond, and having in the range of about 2 up to 20 carbon atoms, and "substituted alkynyl" refers to alkynyl groups further bearing one or more substituents as set forth above;

"aryl" refers to aromatic groups having in the range of 6 up to 14 carbon atoms and "substituted aryl" refers to aryl groups further bearing one or more substituents as set forth above;

"alkylaryl" refers to alkyl-substituted aryl groups and "substituted alkylaryl" refers to alkylaryl groups further bearing one or more substituents as set forth above;

"arylalkyl" refers to aryl-substituted alkyl groups and "substituted arylalkyl" refers to arylalkyl groups further bearing one or more substituents as set forth above;

"arylalkenyl" refers to aryl-substituted alkenyl groups and "substituted arylalkenyl" refers to arylalkenyl further bearing one or more substituents as set forth above;

"arylalkynyl" refers to aryl-substituted alkynyl groups and "substituted arylalkynyl" refers to arylalkynyl further bearing one or more substituents as set forth above;

"aroyl" refers to aryl-carbonyl moiety such as benzoyl and "substituted aroyl" refers to aroyl groups further bearing one or more substituents as set forth above;

"heterocyclic" refers to cyclic (i.e., ring-containing) groups containing one or more heteroatoms (e.g., N, O, S, or the like) as part of the ring structures, and having in the range of 3 up to 14 carbon atoms and "substituted heterocyclic" refers to heterocyclic groups further bearing one or more substituents as set forth above;

"acyl" refers to alkyl-carbonyl groups; and

"halogen" refers to fluoride, chloride, bromide, or iodide groups.

The invention relates to the ability of the α-methylene-γ-butyrolactone moiety in sesquiterpene lactones to be structurally modified by Michael addition with primary and/or secondary amines to form water-soluble amino derivatives. Modification of the parthenolide (1) molecule by this methodology, affords amine adducts that can easily be obtained as different inorganic or organic salts to further increase water solubility. Thus, a novel class of more water-soluble parthenolide analogs is described. When compounds in this class were evaluated for antileukemic activity, it was found that these compounds were either equipotent as, or more potent than the parent compound, parthenolide. More importantly, these novel analogs showed greater cytotoxicity towards leukemia cells than towards normal cells. Thus, the present invention provides a new class of parthenolide derivatives with potent and selective anticancer activities.

In accordance with the present invention, there are provided compounds having the general structure (2):

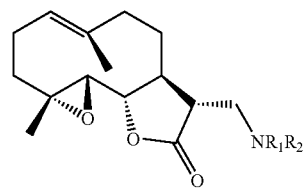

2 wherein:

$R_1$, $R_2$ and $R_3$ may be the same or different;

$R_1$ is selected from hydrogen, alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, perfluoroalkyl, cyano, cyanomethyl, carboxyl, carbamate, sulfonyl, sulfonamide and aryloxyalkyl, or $OR_1$, wherein, 0 is an oxygen;

$R_2$ is selected from hydrogen, alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, perfluoroalkyl, cyano, cyanomethyl, carboxyl, carbamate, sulfonyl, sulfonamide and aryloxyalkyl;

and its pharmaceutically acceptable salts formed with inorganic and/or organic acids, and including its quaternary ammonium salts formed with $R_4Y$; where Y is selected from halogen, tosylate, methanesulfonate, benzenesulfonate, trifluoromethanesulfonate and the like; and $R_4$ is selected from alkyl, substituted alkyl, cycloalkyl, substituted alkyl, hydroxyalkyl, alkenyl, substituted alkenyl, alkynyl, substituted alkynyl, arylalkyl, substituted arylalkyl, arylalkenyl, substituted arylalkenyl, arylalkynyl, substituted arylalkynyl, cyanomethyl, alkyloxyalkyl and aryloxyalkyl.

These acids include: hydrofluoric acid, hydrochloric acid, hydrobromic acid, hydriodic acid, sulfuric acid, nitric acid, phosphoric acid, carbonic acid, boric acid, selenious acid, hydrogen sulfide, phosphomolybdic acid, phosphorous acid, sulfurous acid, citric acid, maleic acid, D-malic acid, L-lactic acid, D-lactic acid, DL-lactic acid, oxalic acid, methanesulfonic acid, valeric acid, oleic acid, lauric acid, paratoluenesulfonic acid, 1-naphthalensulfonic acid, 2-naphthalensulfonic acid, phthalic acid, tartaric acid, L-malic acid, DL-malic acid, malonic acid, succinic acid, fumaric acid, glycolic acid, thioglycolic acid, glycine, sarcocine, sulfonic acid, nicotinic acid, picolinic acid, isonicotinic acid, benzoic acid and substituted benzoic acid which refers to the benzene ring further bearing one or more substituents as set forth below, and XCOOH whereas X is selected from is selected from hydrogen, alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, perfluoroalkyl, cyano, cyanomethyl, carboxyl, carbamate, sulfonyl, sulfonamide and aryloxyalkyl, or —OX and —SX.

Presently preferred compounds of the invention are those wherein $R_1$ is hydrogen or optionally substituted lower alkyl; and $R_2$ is optionally substituted lower alkyl.

According to one embodiment of the invention, $R_1$ and $R_2$ are each —$CH_3$.

In another embodiment, $R_1$ and $R_2$ are each —$CH_2CH_3$.

In a further embodiment, $R_1$ is —$CH_2CH_3$ and $R_2$ is —$CH_3$.

In yet another embodiment of the invention, $R_1$ is —$CH_2CH_2CH_3$ and $R_2$ is —$CH_3$.

According to another embodiment, $R_1$ is —$CH(CH_3)_2$ and $R_2$ is —$CH_3$.

In an alternative embodiment of the present invention, $R_1$ and $R_2$ can combine with N to form a ring system. Examples of such combination include —$CH_2(CH_2)_nCH_2$—; where n is selected from 0 to 5. These ring systems can also have one or more substituents selected from alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, perfluoroalkyl, cyano, cyanomethyl, carboxyl, carbamate, sulfonyl, sulfonamide, aryloxyalkyl and halogen as set forth above.

This ring system can also be —$CH_2(CH_2)_nCH_2Z$—; where Z is O, S, Se, Si, P, —CO—, —SO—, —$SO_2$—, —PO—; and —$CH_2(CH_2)_nCH_2$— are the groups as set forth above.

Alternatively, this ring system can be —$(CH_2)_a$-Z-$(CH_2)_b$—; where a and b are the same or different and are from 1 to 4; and Z is O, N, S, Se, Si, P, —CO—, —SO—, —$SO_2$— or —PO—. This ring system can also be a uracil ring and its derivatives with one or more substituents. These ring systems can also have one or more substituents connected to the carbon atom(s) and/or Z. The substituent is selected from alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, perfluoroalkyl, cyano, cyanomethyl, carboxyl, carboxylate, carboxaldehyde, carboxamide, carbamate, hydroxy, alkoxy, isocyanate, isothiocyanate, nitro, nitroso, nitrate, sulfate, sulfonyl, sulfonamide, thiol, thioalkyl, aryloxyalkyl and halogen as set forth above.

Any of the above ring systems comprising $NR_1R_2$ may optionally be fused with another ring to form an optionally substituted bicyclic or tricyclic ring system, each of the rings optionally comprising one or more heteroatoms. Preferred ring systems include aziridin-1-yl, azetidin-1-yl, pyrrolidin-1-yl, piperidin-1-yl, homopiperidyn-1-yl and heptamethyleneimin-1-yl, each being optionally substituted with one or more substituents as set forth above.

Exemplary compounds of the present invention include:
11βH,13-Dimethylaminoparthenolide;
11βH,13-Diethylaminoparthenolide;
11βH,13-(tert-Butylamino)parthenolide;
11βH,13-(Pyrrolidin-1-yl)parthenolide;
11βH,13-(Piperidin-1-yl)parthenolide;
11βH,13-(Morpholin-1-yl)parthenolide;
11βH,13-(4-Methylpiperidin-1-yl)parthenolide;
11βH,13-(4-Methylpiperazin-1-yl)parthenolide;
11βH,13-(Homopiperidin-1-yl)parthenolide;
11βH,13-(Heptamethyleneimin-1-yl)parthenolide;
11βH,13-(Azetidin-1-yl)parthenolide; and
11βH,13-Diallylaminoparthenolide.

Those of skill in the art recognize that invention comprises compounds that may contain one or more chiral centers on the —$NR_1R_2$ group, and thus can exist as racemic mixtures as pure diastereomers, or as pure enantiomers. For many applications, it is preferred to carry out stereoselective synthesis and/or to subject the reaction product to appropriate purification steps so as to produce substantially stereochemically pure or optically pure materials. Suitable stereoselective synthetic procedures for producing stereochemically pure or optically pure materials are well known in the art, as are procedures for resolving racemic mixtures into their optically pure enantiomers.

The —$NR_1R_2$ group may also be a primary amine or part of another anti-cancer drug moiety, constituting the formation of a "duplex aminoparthenolide analogue (Structure 3 and Scheme II below) or the covalent union of parthenolide with basic nitrogen-containing synergistic anticancer drug molecules such as 5-fluorouracil, cytarabine, mytomycin C, Doxorubicin, Daunorubicin, (Scheme III, formula 4 below as a representative example), respectively. Thus, the present invention further provides compounds of the formula (3):

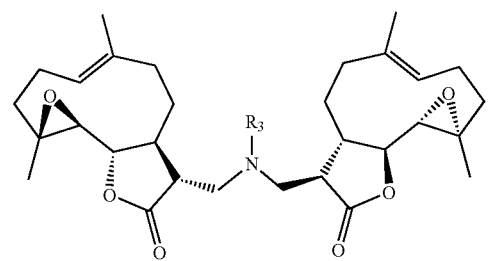

3 wherein $R_3$ is selected from hydrogen, alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, perfluoroalkyl, cyano, cyanomethyl, carboxyl, carbamate, sulfonyl, sulfonamide and aryloxyalkyl, or $OR_1$, wherein O is an oxygen;

and its pharmaceutically acceptable salts formed with inorganic and/or organic acids, and its quaternary ammonium salts formed with $R_4Y$. Preferred $R_3$ groups include H, alkyl, aralkyl, alkenyl, alkynyl, cycloalkyl, cycloalkenyl, cycloalkynyl, alkylaryl, alkenylaryl and alkynylaryl.

In accordance with another embodiment of the invention, the methods for the preparation of the amino analogs described in this invention are disclosed in Schemes I and II.

Scheme I

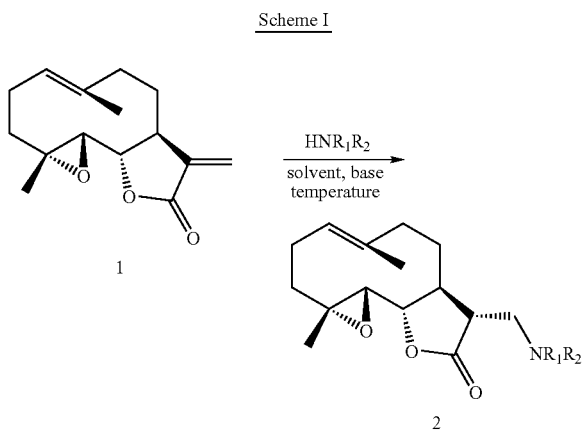

Scheme II

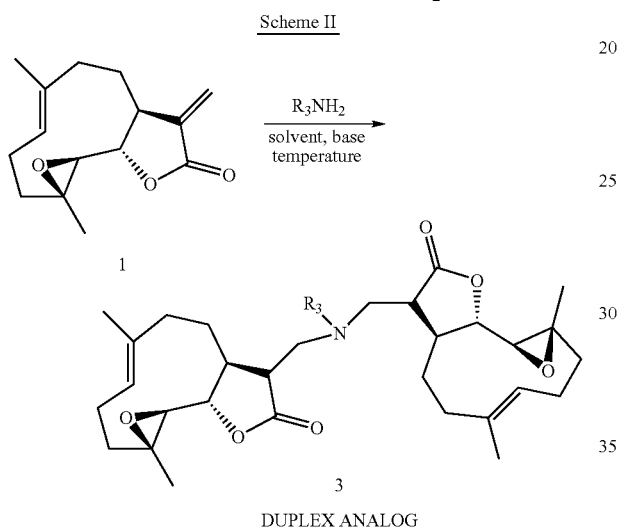

DUPLEX ANALOG

In the above scheme, $R_1$ and $R_2$ are defined as previously; and the solvent is selected from a low alkyl alcohol, such as methanol, ethanol, propanol, isopropanol, n-butanol, tert-butanol, and chloroform, methylene chloride, benzene, toluene, tetrahydrofuran, dioxane, 1,2-dimethoxyethane, pyridine, carbon tetrachloride, diethyl ether, tert-butyl methyl ether and/or the mixture of two or more of the solvents listed above. The base is selected from a low trialkylamine, such as trimethylamine, triethylamine, tripropylamine, and tributylamine, and pyridine, 2-, 3-, and 4-picolines, 2-, 3-, and 4-dimethylaminopyridines. The temperature is selected from −20° C. to 130° C. The reaction time required to effect the desired coupling reaction can vary widely, typically falling in the range of 30 min to 24 hours. Purification can be achieved by a variety of techniques, such as, liquid chromatography through neutral or basic silica gel, bonded silica gel phases such as octadecylsilica, octylsilica and the like, cellulose or alumina with the solvent such as, for example, the mixture of chloroform and methanol or ethanol, the mixture of methylene chloride and methanol or ethanol, the mixture of hexane and acetone or acetonitrile or methanol or ethanol or isopropanol, the mixture of diethyl ether and acetone or acetonitrile or methanol or ethanol or isopropanol; and recrystallization using normal organic solvent or solvent mixture, such as methanol, ethanol, propanol, isopropanol, tert-butanol, acetonitrile, diethyl ether, chloroform, methylene chloride and the mixture of two or more solvents listed above. The purity of the invention compounds prepared is assessed by mass spectrometry, nuclear magnet resonance spectrometry and elemental combustion analysis.

Scheme III

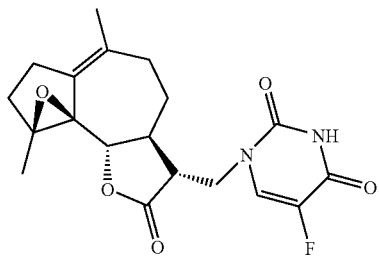

5-Fluorouracil-Parthenolide Codrug

Furthermore, in accordance with still another embodiment of the present invention, the methods for the preparation of the invention salts are disclosed in Schemes IV and V.

Scheme IV

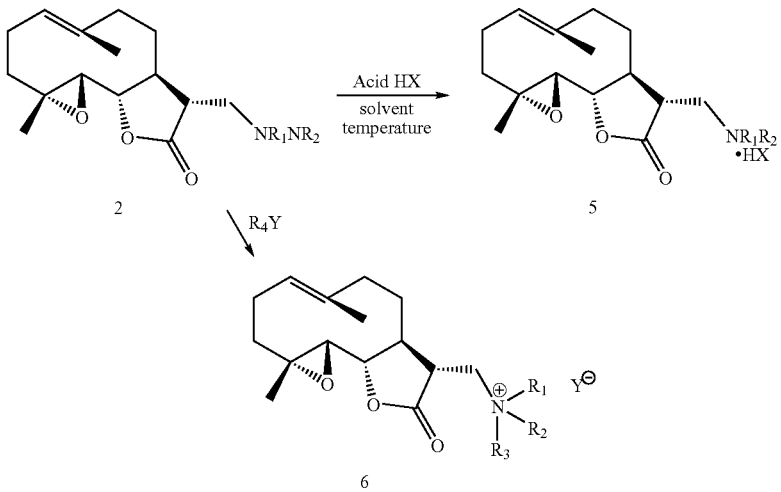

In these schemes, HX is selected from hydrochloride, hydrobromide, hydroiodide, perchlorate, sulfate, hemisulfate mesylate, toluenesulfonate, benzenesulfonate, succinate, hemisuccinate, fumarate, acetate, hemifumarate, maleate, maleate, citrate, oxalate, malonate, propionate and benzoate; Y⊖ is selected from halide (fluoride, chloride, bromide, iodide), methylsulfonate, toluenesulfonate, benzenesulfonate and sulfate; and the solvent is selected from a low alkyl alcohol, such as diethyl ether, methanol, ethanol, propanol, isopropanol, n-butanol, tert-butanol, and chloroform, methylene chloride, benzene, toluene, tetrahydrofuran, dioxane, 1,2-dimethoxyethane, pyridine, carbon tetrachloride, tert-butyl methyl ether, acetone and/or the mixture of two or more of the solvents listed above. The temperature is selected from −20° C. to 50° C. Purification can be achieved by recrystallization using normal organic solvent or solvent mixture, such as methanol, ethanol, acetone, propanol, isopropanol, t-butanol, acetonitrile, diethyl ether, chloroform, methylene chloride and the mixture of two or more solvents listed above.

Also part of the invention are analogues of the same type as above for the following structurally related parthenolide-like constituents: costunolide, dehyrocostuslactone, alantolactone, isoalantolactone, amino-3-oxo-isoalantolactone, helenalin, 11,13-dihydrohelenalin, aminocyanaropicrin, aminodesacylcyanaropicrin, (+)-aminoreyonosin, aminosantamarin, aminosoulangianolide, and aminoisotelekin (see Scheme VI).

Scheme VI

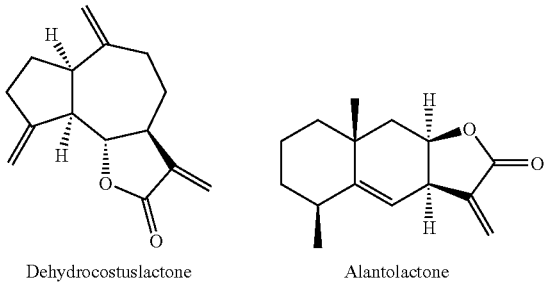

Dehydrocostuslactone      Alantolactone

Scheme V

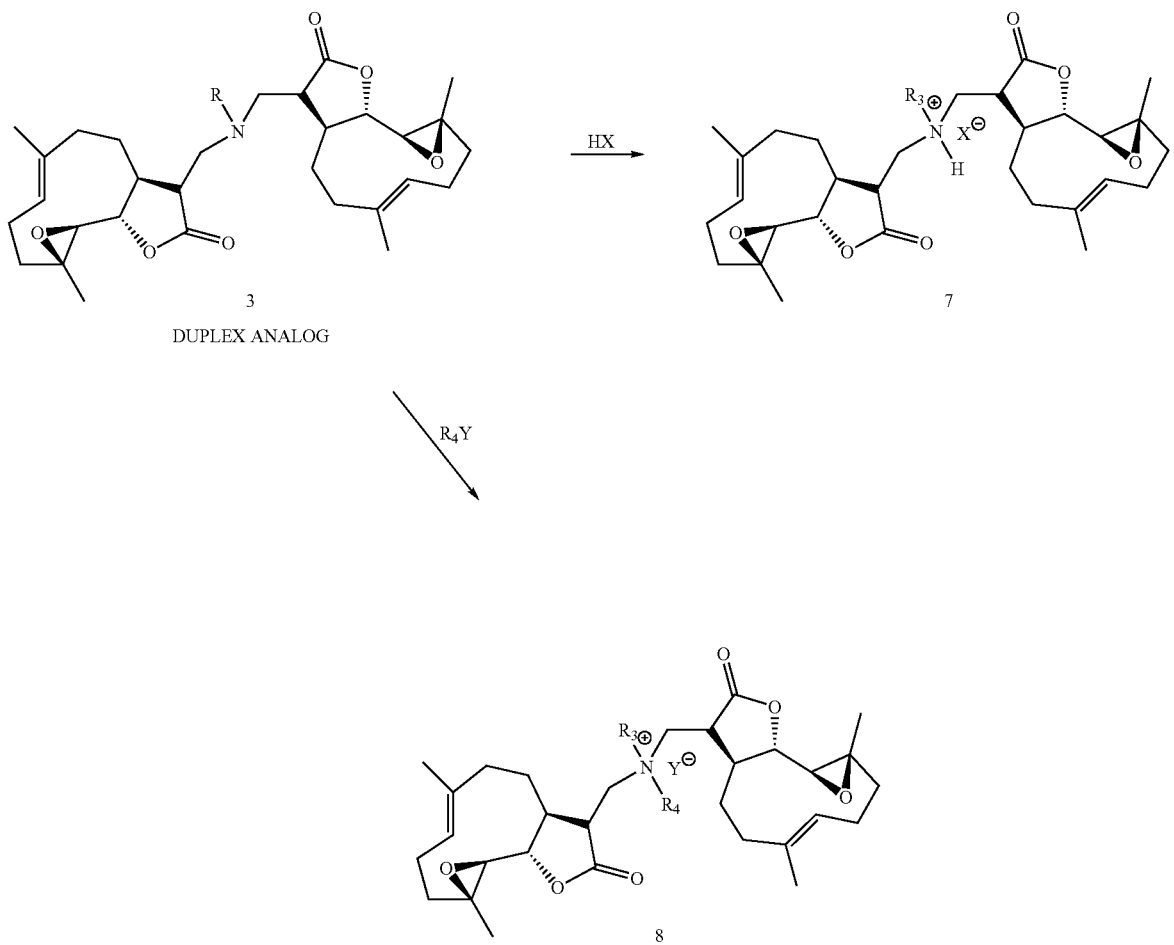

-continued

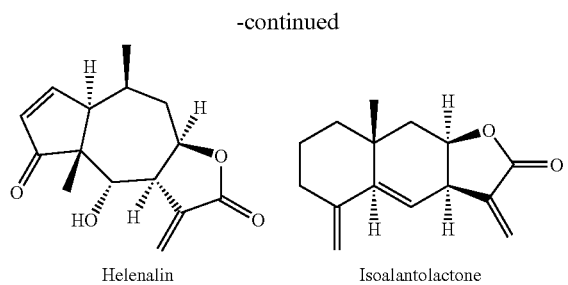

Helenalin
Isoalantolactone

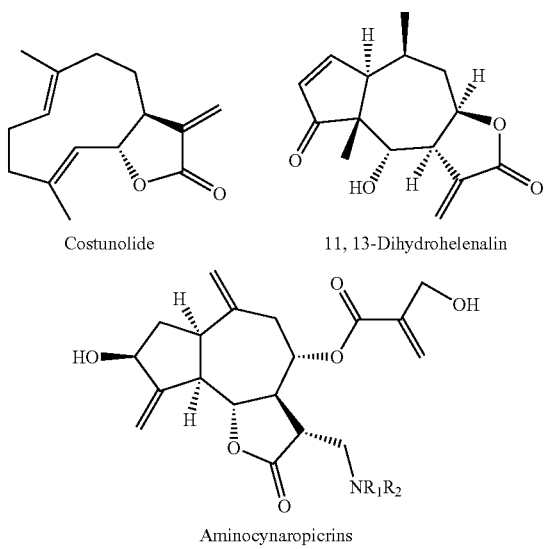

Costunolide
11, 13-Dihydrohelenalin

Aminocynaropicrins

Aminodesacylcynaropicrins

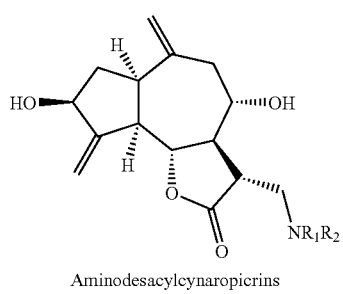

(+)-Aminoreynosins

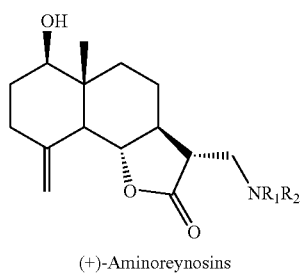

Aminosantamarins

-continued

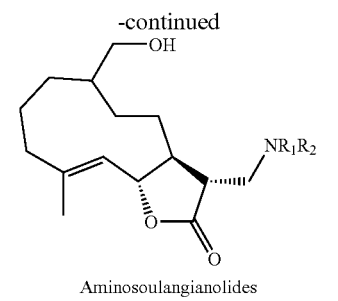

Aminosoulangianolides

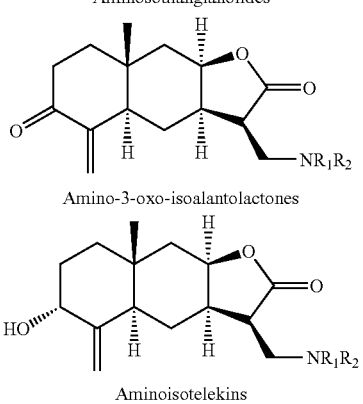

Amino-3-oxo-isoalantolactones

Aminoisotelekins

The compounds described herein are useful for treating cancer. Cancers treatable by the present therapy include the solid and hematological tumors, such as prostate cancer, ovarian cancer, breast cancer, brain cancer and hepatic cancer, comprising administering to a mammal afflicted with said cancer an amount of parthenolide derivative effective to inhibit the viability of cancer cells of said mammal. The parthenolide derivative may be administered as primary therapy, or as adjunct therapy, either following local intervention (surgery, radiation, local chemotherapy) or in conjunction with at least one other chemotherapeutic agent. discussed hereinabove, as well as the solid tumors disclosed in U.S. Pat. No. 5,514,555. Hematological cancers, such as the leukemias are disclosed in the Mayo Clinic Family Health Book, D. E. Larson, ed., William Morrow, N.Y. (1990) and include CLL, ALL, CML and the like.

Within another aspect of the present invention, methods are provided for inhibiting angiogenesis in patients with non-tumorigenic, angiogenesis-dependent diseases, comprising administering a therapeutically effective amount of a composition comprising parthenolide derivative to a patient with a non-tumorigenic angiogenesis-dependent disease, such that the formation of new blood vessels is inhibited. Within other aspects, methods are provided for inhibit reactive proliferation of endothelial cells or capillary formation in non-tumorigenic, angiogenesis-dependent diseases, such that the blood vessel is effectively occluded. Within one embodiment, the anti-angiogenic composition comprising parthenolide derivative is delivered to a blood vessel which is actively proliferating and nourishing a tumor.

In addition to tumors, numerous other non-tumorigenic angiogenesis-dependent diseases, which are characterized by the abnormal growth of blood vessels, may also be treated with the anti-angiogenic parthenolide derivative compositions, or anti-angiogenic factors of the present invention. Anti-angiogenic parthenolide derivative compositions of the present invention can block the stimulatory effects of angiogenesis promoters, reducing endothelial cell division, decreasing endothelial cell migration, and impairing the activity of the proteolytic enzymes secreted by the endothelium. Representative examples of such non-tumorigenic angiogenesis-dependent diseases include corneal neovascularization, hypertrophic scars and keloids, proliferative diabetic retinopathy, arteriovenous malformations, atherosclerotic plaques, delayed wound healing, hemophilic joints, nonunion fractures, Osler-Weber syndrome, psoriasis, pyogenic granuloma, scleroderma, trachoma, menorrhagia, retrolental fibroplasia and vascular adhesions. The pathology and treatment of these conditions is disclosed in detail in published PCT application PCT/CA94/00373 (WO 95/03036), at pages 26–36. Topical or directed local administration of the present compositions is often the preferred mode of administration of therapeutically effective amounts of parthenolide derivative, i.e., in depot or other controlled release forms.

Anti-angiogenic compositions of the present invention may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labelled monoclonal antibody which recognizes active endothelial cells.

The magnitude of a prophylactic or therapeutic dose of parthenolide derivative, an analog thereof or a combination thereof, in the acute or chronic management of cancer, i.e., prostate or breast cancer, will vary with the stage of the cancer, such as the solid tumor to be treated, the chemotherapeutic agent(s) or other anti-cancer therapy used, and the route of administration. The dose, and perhaps the dose frequency, will also vary according to the age, body weight, and response of the individual patient. In general, the total daily dose range for parthenolide derivative and its analogs, for the conditions described herein, is from about 0.5 mg to about 2500 mg, in single or divided doses. Preferably, a daily dose range should be about 1 mg to about 100 mg, in single or divided doses, most preferably about 5–50 mg per day. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

Any suitable route of administration may be employed for providing the patient with an effective dosage of parthenolide derivative (e.g., oral, sublingual, rectal, intravenous, epidural, intrethecal, subcutaneous, transcutaneous, intramuscular, intraperitoneal, intracutaneous, inhalation, transdermal, nasal spray, nasal gel or drop, and the like). While it is possible that, for use in therapy, parthenolide derivative or its analogs may be administered as the pure chemicals, as by inhalation of a fine powder via an insufflator, it is preferable to present the active ingredient as a pharmaceutical formulation. The invention thus further provides a pharmaceutical formulation comprising parthenolide derivative or an analog thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the agent from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. The polymer matrix can be coated onto, or used to form, a medical prosthesis, such as a stent, valve, shunt, graft, or the like.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer.RTM. (Wintrop) and the Medihaler.RTM. (Riker).

For topical administration to the eye, the compounds can be administered as drops, gels (U.S. Pat. No. 4,255,415), gums (see U.S. Pat. No. 4,136,177) or via a prolonged-release ocular insert.

The invention will now be described in greater detail by reference to the following non-limiting examples.

EXAMPLES

Example 1

General Synthetic Procedure for the Preparation of 11βH,13-Substituted Aminoparthenolides A mixture of parthenolide (100 mg, 0.4 mmol), the appropriate primary amine or secondary amine (2 mmol), and triethylamine (1 to 2 ml) in 30 ml of anhydrous ethanol was stirred at a specific temperature ranging from ambient temperature to the temperature of the refluxing solvent utilized, or was left to stand in the refrigerator (−20° C. to 4° C.) overnight for 24 hours. Ethanol, triethylamine and/or the appropriate volatile amine were then evaporated under vacuum in a rotavapor. The resulting residue was subjected to silica gel column chromatographic purification using chloroform-methanol or methylene chloride-methanol mixed solvent as the mobile phase. NMR (Varian, 300 MHz and 400 MHz) and GC/MS (Agilent, 6890GC and 5973MSD) analysis methodologies were utilized to assure the identity and purity of the synthetic compounds.

Example 2

11βH,13-Dimethylaminoparthenolide

Parthenolide (100 mg, 0.4 mmol), dimethylamine(2M in methanol, 1 ml), triethylamine (2 ml), ethanol (30 ml) were refluxed overnight. After column purification, 109 mg of pale yellow 11βH,13-dimethylaminoparthenolide was obtained (Yield: 93%).

Example 3

11βH,13-Diethylaminoparthenolide

Parthenolide (100 mg, 0.4 mmol), diethylamine (200 mg, 2.7 mmol), triethylamine (2 ml), ethanol (30 ml) were refluxed overnight. After column purification, 114 mg of yellow 11H,13-Diethylaminoparthenolide was obtained (Yield: 88%).

Example 4

Preparation of Salts of Aminoparthenolide Derivatives

The aminoparthenolide derivative was dissolved in anhydrous ether and to this solution was added the corresponding acid in ether or ethanol. The mixture was kept in the refrigerator (4° C.) overnight. The crystals formed was filtered and dried under vacuum, or submitted to further recrystallization, if needed.

Example 5

Preparation of 11βH,13-(piperidin-1-yl)parthenolide hydrochloride

11βH,13-(piperidin-1-yl)parthenolide (5 mg) was dissolved in 2 ml of dry ether. Hydrochloride in ether (1M, 0.015 ml) was added to the ether solution until the solution became cloudy; then more ether was added and the mixture was heated to obtain a clear solution. The mixture was left in refrigerator (4° C.) for more than 24 hours. The white crystals that formed were filtered through filter paper, and dried under vacuum overnight (Yield: 18%).

Example 6

Preparation of 11βH, 13-dimethylaminoparthenolide maleate

To 11βH,13-dimethylaminoparthenolide (30 mg, 0.1 mmol) in anhydrous ethanol (5 ml) was added maleic acid (12 mg, 0.1 mmol) in 3 ml of anhydrous ethanol. The solution was shaken well and filtered through a regular filter paper. The clear solution was left in the refrigerator for a week. The white crystals formed were obtained by filtration, dried in a desiccator under vacuum with anhydrous $CaCl_2$ (Yield: 55%).

Example 7

Preparation of 11βH, 13-Dimethylaminoparthenolide methiodide

To 11βH,13-dimethylaminoparthenolide (30 mg, 0.1 mmol) in anhydrous methanol (5 ml) was added iodomethane (90 mg, 0.6 mmol) in methanol (1 ml). The clear solution was shaken and stored at room temperature. After three days, the methanol was evaporated, the pale yellow residue was dried in a desiccator under vacuum, over anhydrous $CaCl_2$. Recrystallization from acetone-ether afforded pale yellow crystals (Yield: 86%).

Example 8

11βH,13-(4-Methylpiperidin-1-yl)parthenolide methiodide: To 11βH,13-(4-methylpiperidin-1-yl)parthenolide (35 mg, 0.1 mmol) in anhydrous methanol (5 ml) was added iodomethane (90 mg, 0.6 mmol) in methanol (1 ml). The clear solution was shaken and stored at room temperature. After three days, the methanol was evaporated, the pale yellow residue was dried in a desiccator under vacuum, over anhydrous $CaCl_2$. Recrystallization from acetone-ether afforded pale yellow crystals (Yield: 79%).

Example 9

Assay for Antileukemic Activity

For apoptosis analysis, one million primary acute myelogenous leukemia cells were washed with cold PBS and resuspended in 200 microliters of Annexin binding buffer (10 mM HEPES/NaOH pH 7.4; 140 mM NaCl; 2.5 mM $CaCl_2$). Annexin V-FITC (Pharmingen) and 0.25 mg/ml 7-AAD (7-aminoactinomycin D, Molecular Probes, CA) were added and the tubes were incubated at room temperature in the dark for 15 minutes. Cells were then diluted with 200 microliters of Annexin binding buffer and analyzed immediately by flow cytometry. Viable cells were identified as failing to label with Annexin V or 7-AAD. Cells beginning to die label with Annexin V, and as membrane integrity is lost, will also label with 7-AAD. For each parthenolide derivative, the percentage of viable cells was determined after 24 hours of culture at a 10 micromolar concentration. Data are normalized to untreated control specimens. The data are in Table 1 for aminoparthenolide derivatives and Table 2 for the salts of some aminoparthenolides.

Healthy human bone marrow cells were used in the above assay to test the cytotoxicity of parthenolide. Eighty-five percent of the normal cells survived 10 μM of parthenolide. All the aminoparthenolides evaluated afforded similar results to parthenolide, i.e. the survival rate of healthy human bone marrow cells was over 85% at a concentration of 10 μM.

TABLE 1

Aminoparthenolides and their antileukemic activity

| Compound | Reactants and Solvent | Reaction Conditions | Yield (%) | Antileukemic activity |
|---|---|---|---|---|
| 11βH,13-Dimethylaminoparthenolide | Parthenolide (100 mg), dimethylamine (2 M in methanol, 1 ml), triethylamine(2 ml), ethanol (30 ml) | Refluxing overnight | 93 | 5 μM, 31%<br>10 μM, 90%<br>20 μM, 95% |
| 11βH,13-Diethylaminoparthenolide | Parthenolide (100 mg), diethylamine (200 mg, 2.7 mmol), triethylamine (2 ml), ethanol (30 ml) | Refluxing overnight | 88 | 10 μM, 60% |
| 11βH,13-(tert-Butylamino)parthenolide | Parthenolide (20 mg), tert-butylamine (0.2 ml), triethylamine (0.4 ml), ethanol (5 ml) | Refluxing 10 hours | 39 | 10 μM, 20% |
| 11βH,13-(Pyrrolidin-1-yl)parthenolide | Parthenolide (30 mg), pyrrolidine (0.2 ml), triethylamine (0.2 ml), ethanol (5 ml) | Refluxing 12 hours | 80 | 5 μM, 23%<br>10 μM, 85%<br>20 μM, 95% |
| 11βH,13-(Piperidin-1-yl)parthenolide | Parthenolide (250 mg), piperidine (1 ml), triethylamine (5 ml), ethanol (100 ml) | Refluxing overnight | 86 | 2.5 μM, 71%<br>5 μM, 91% |

TABLE 1-continued

Aminoparthenolides and their antileukemic activity

| Compound | Reactants and Solvent | Reaction Conditions | Yield (%) | Antileukemic activity |
|---|---|---|---|---|
| 11βH,13-(Morpholin-1-yl)parthenolide | Parthenolide (100 mg), morpholine (0.5 ml), triethylamine (2 ml), ethanol (30 ml) | Refluxing overnight | 91 | 5 μM, 5% 20 μM, 20% |
| 11βH,13-(4-Methylpiperidin-1-yl)parthenolide | Parthenolide (100 mg), 4-methylpiperidine (0.5 ml), triethylamine (2 ml), ethanol (30 ml) | Refluxing overnight | 89 | 10 μM, 83% |
| 11βH,13-(4-Methylpiperazin-1-yl)parthenolide | Parthenolide (30 mg), 4-methylpiperazine (0.2 ml), triethylamine (1 ml), ethanol (20 ml) | Refluxing overnight | 74 | 10 μM, 7% |
| 11βH,13-(Homopiperidin-1-yl)parthenolide | Parthenolide (100 mg), homopiperidine (500 mg), triethylamine (2 ml), ethanol (30 ml) | Refluxing overnight | 82 | 10 μM, 40% |
| 11βH,13-(Heptamethyleneimin-1-yl)parthenolide | Parthenolide (100 mg), heptamethyleneimin (500 mg), triethylamine (2 ml), ethanol (30 ml) | Refluxing overnight | 74 | 10 μM, 10% |
| 11βH,13-(Azetidin-1-yl)parthenolide | Parthenolide (100 mg), azetidine (100 mg), triethylamine (2 ml), ethanol (20 ml) | Stirred at room temperature 2 days | 93 | |
| 11βH,13-Diallylaminoparthenolide | Parthenolide (100 mg), diallylamine (200 mg), triethylamine (2 ml), ethanol (30 ml) | Refluxing overnight | 57 | |

TABLE 2

Aminoparthenolide salts and their antileukemic activity

| Compound | Reactants and Solvent | Reaction Conditions | Yield (%) | Antileukemic activity |
|---|---|---|---|---|
| 11βH,13-Dimethylaminoparthenolide hydrochloride | 11βH,13-Dimethylaminoparthenolide (10 mg), HCl in ether (1 M, 0.03 ml) | Refrigerator, 24 hours | 72 | |
| 11βH,13-(Pyrrolidin-1-yl)parthenolide hydrochloride | 11βH,13-(Pyrrolidin-1-yl)parthenolide (5 mg), HCl in ether (1 M, 0.015 ml) | Refrigerator, 24 hours | 10 | 10 μM, 85% |
| 11βH,13-(Piperidin-1-yl)parthenolide hydrochloride | 11βH,13-(Piperidin-1-yl)parthenolide (5 mg), HCl in ether (1 M, 0.015 ml) | Refrigerator, 24 hours | 18 | 10 μM, 88% |
| 11βH,13-(4-Methylpiperidin-1-yl)parthenolide hydrochloride | 11βH,13-(4-Methylpiperidin-1-yl)parthenolide (50 mg), HCl in ether (1 M, 0.15 ml) | Refrigerator, 4 days | 38.3 | 10 μM, 62% |
| 11βH,13-Dimethylaminoparthenolide maleate | 11βH,13-Dimethylaminoparthenolide (30 mg), maleic acid (12 mg), ethanol (8 ml) | Room temperature for 1 week | 55 | |
| 11βH,13-Dimethylaminoparthenolide methiodide | 11βH,13-Dimethylaminoparthenolide (30 mg), added iodomethane (90 mg), methanol (6 ml) | Room temperature for 3 days | 86 | |

TABLE 2-continued

Aminoparthenolide salts and their antileukemic activity

| Compound | Reactants and Solvent | Reaction Conditions | Yield (%) | Antileukemic activity |
|---|---|---|---|---|
| 11βH,13-(4-Methylpiperidin-1-yl)parthenolide methiodide | 11βH,13-(4-Methylpiperidin-1-yl)parthenolide (70 mg), iodomethane (200 mg), methanol (12 ml) | Room temperature for 3 days | 79 | |

Example 10

Analysis of Parthenolide and Dimethylaminoparthenolide (DMAPT) Using Human-Mouse Xenografts To assess the effect of parthenolide on primary human stem cell populations, experiments were conducted using transplantation into immune deficient NOD/SCID mice. Successful engraftment of NOD/SCID bone marrow at 6–8 weeks post-transplant has been shown to be a measure of stem cell content for human hematopoietic cell populations (Lapidot et al., *J Mol Med.* 1997; 75:664–673; Dick, *Curr Opin Hematol.* 1996; 3:405–409). For each experiment, cryopreserved mononuclear cell specimens from normal or AML donors were thawed, and treated in vitro with 7.5 micromolar parthenolide for 12–18 hours. Following culture, 5–10 million cells/animal were injected intravenously into sublethally irradiated (300 Rad) NOD/SCID mice. After 6–8 weeks, animals were sacrificed and bone marrow was analyzed for the presence of human cells using flow cytometry as previously described (Guzman et al., *Proc Natl Acad Sci USA* 2002; 99:16220–162253). Human specific antibodies for CD45 were used to assess the level of total engraftment.

In three independent experiments, the level of engraftment for parthenolide-treated AML cells was dramatically reduced, which indicates a direct effect on the AML stem cell compartment. In contrast, no reduction in engraftment was detected for parthenolide-treated normal specimens, thus showing the parthenolide does not target normal hematopoietic stem cells. Similarly, treatment of AML cells with 7.5 micromolar DMAPT also yielded a strong reduction in NOD/SCID engraftment while treatment of normal cells showed no significant effects.

Example 11

MTS-PMS Assay

Details of MTS-PMS assay—96-well U-bottomed plate (Becton Dickinson Labware, Franklin Lakes, N.J.) at a concentration of 5,000 cells per 50 microliters (mL) of media and incubated in 5% $CO_2$ at 37° C. for 24 hours. Varying compound concentrations in 50 mL of media were added to the media 24 hours later. Colorimetric readings were obtained using the MTS/PMS system and an ELISA plate reader, after 48 hours of exposure to DMAPT. The readings obtained for each concentration tested were from an average of eight wells. Each experiment was expressed as a percentage of the solvent control and completed at least three times with consistent results. The results presented are an average of three experiments. The hormone refractory prostate cancer cell line CWR22Rv1 was treated with increasing concentrations of parthenolide and derivatives for three hours (FIG. 1). Cellular proliferation was reduced by 50% by 5 μm in the MTS-PMS assay.

Example 12

Clonogenic Assay

Initially, 100 cells growing in log phase are plated per 3 ml of media in each well of six well plate. After 24 hrs of plating of the cells, DMAPT was added at varying concentrations. At 24 and 96 hours after addition of drug, the media is changed. Hence, the cells are only exposed to the drug for 24 hrs only. When cell colonies appear at Day 15 they are stained by Sure Stain Dye for 15 and counted.

Example 13 cDNA Array Analysis

Total cellular RNA was extracted from the human monocyte cell line THP-1 under three conditions 2 hours after Time 0:
1) Control was added at Time 0
2) Lipopolysacchride (10 nM) was added at Time plus one (1) hour
3) At Time 0, 10 micromoles of DMAPT was added and then at Time+1 LPS (10 nM) was added.

RNA was extracted using RNeasy Min Kit (Qiagen, USA) according to the manufacturer's instructions. The Human Drug Targets for Inflammation and Immunomodulation Q series GE array kit (HS-048-12) was obtained from Super-Array Bioscience Corporation (Frederick, Md.). The kit determines expression of 96 genes that are associated with inflammation. RNA from respective samples was used as a template to generate biotin labeled cDNA probes using GEArray Ampolabelling RT kit (SuperArray, Bioscience Corp., USA). The cDNA probes corresponding to the mRNA population were then denatured and hybridization was carried out in GEHyb solution to nylon membranes spotted with gene specific fragments. Membranes were then washed in 2×SSC, 1% SDS twice for 15 minutes each, followed by 0.1 SSC, 0.5% SDS twice for 15 minutes each. Chemiluminescence was used to visualize the expression levels of each transcript and the results were quantified with the GEArray Analyzer. The change in a given gene transcript was estimated by normalizing the signal intensities with the signal derived from PPIA and with minimum background subtraction.

As can be seen in Table 3, transcription of 25 genes was increased after pre-treatment with LPS. More importantly pretreatment with DMAPT prevented or blunted the increase in gene transcription induced by LPS. For example, the transcription of tumor necrosis factor (TNF), released in septic shock, is increased by 3 fold (298%) when treated with LPS. Pretreatment with DMAPT however prevents transcription of LPS and in fact decreases its production to 2% of control. Similarly, transcription of cyclo-oxygenase-2, the target of classical non-steroidal anti-inflammatory agents, was increased 1.5 fold (150%). In the presence of DMAPT, the gene expression not only prevented the increase by LPS but decreased it to 30% (0.7) of solvent control.

TABLE 3 cDNA Array Analysis

| Gene | LPS Treatment for 1 hour: % Change of Gene | DMAPT Pre-treatment for 2 hours then 1 hour Treatment of LPS % Change of Genes |
|---|---|---|
| CD28 antigen (Tp44) | 23 | 0.814 |
| CD3G antigen, gamma polypeptide (TiT3 complex) | 14 | 0.6 |
| Colony stimulating factor 2 (granulocyte-macrophage) | 26 | 0.926 |
| Intercellular Adhesion Molecule 1 | 257 | 58 |
| Interleukin 13 | 93 | 0.64 |
| Interleukin 1 receptor, type I | 10 | 0.33 |
| Interleukin 1 receptor, type II | 326 | 0.74 |
| Nitric oxide synthase 2A (inducible) | 226 | 48 |
| Phosphodiesterase 4A, cAMP-specific | 14 | 0.46 |
| Phosphodiesterase 4B, cAMP-specific | 220 | 0.59 |
| Phospholipase A2, group IB (pancreas) | 114 | 0.57 |
| Phospholipase A2, group IVC | 350 | 0.89 |
| Phospholipase A2, group VII | 129 | 0.05 |
| Phospholipase C, gamma 1 | 342 | 0.24 |
| Peroxisome proliferative activated receptor, gamma | 49 | 0.48 |
| Platelet-activating factor receptor | 32 | 0.002 |
| Prostaglandin D2 receptor (DP) | 35 | 0.17 |
| Prostaglandin F receptor (FP) | 879 | 1.46 |
| Cyclooxygenase 1 | 176 | 0.731 |
| Cyclooxygenase 2 | 152 | 0.7 |
| Thromboxane A synthase 1 | 283 | 0.07 |
| Tumor necrosis factor (TNF superfamily, member 2) | 298 | 0.02 |
| Tumor necrosis factor (ligand), superfamily member 13b | 217 | 0.89 |
| Tumor necrosis factor (ligand) superfamily, member 5 | 692 | 23 |
| Vascular cell adhesion molecule 1 | 154 | 0.02 |

Example 14

Parthenolide and Derivative Assay Activity

Presented herein is data demonstrating that: compounds of the present invention reduce the viability of and increases sensitivity to chemotherapy of lung cancer, prostate, and breast cancer cell lines as well as decrease inflammation by decreasing cytokines as evidenced by decreased genes in human monocytes.

The hormone refractory prostate cancer cell line CWR22Rv1 was treated with increasing concentrations of parthenolide derivatives DMAPT, PIPT and 4MEPT for three hours. Cellular proliferation was reduced by up to 80% at 2 um in the clonogenic assay and by 50% by 5 μ/m in the MTS-PMS assay (FIG. 1).

Figure 2:
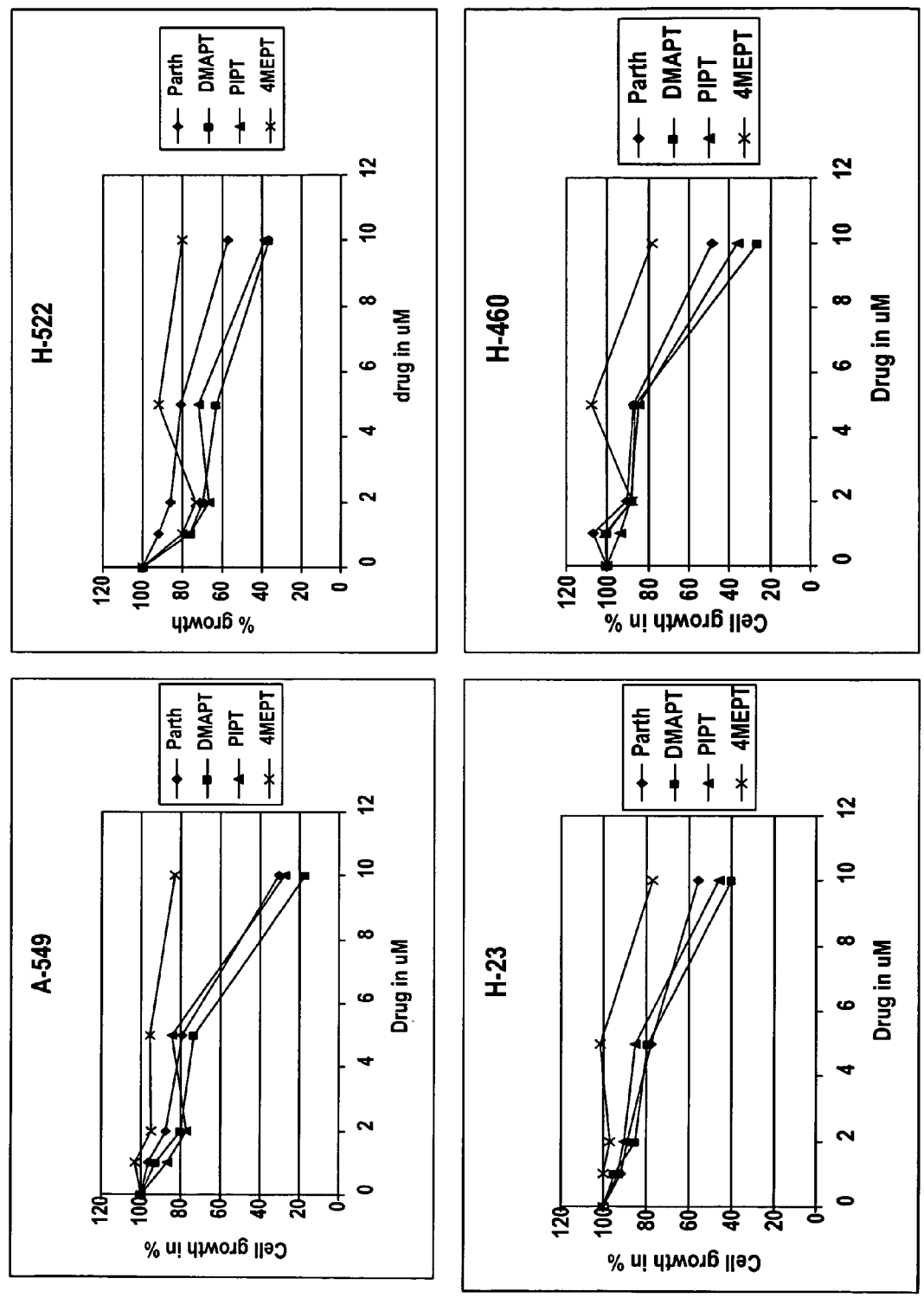
FIG. 2 shows the effectiveness of parthenolide and derivatives of the present invention in the MTS-PMS assay against lung cancer cell lines A-549, H522, H-23 and H-460.

Cellular proliferation was measured in the MTS-PMS assay of the four lung cancer cell lines to parthenolide and derivatives PipPT ((11βH, 13-(piperidin-1-yl)parthenolide), 4MePipPT (11βH, 13-(4-methylpiperidin-1-yl)parthenolide") and MAPT. Parthenolide and its derivatives inhibited cellular proliferation in a dose dependent manner between 2 and 10 μM with 70% inhibition at 10 μM in A549, 50% in H460, 40% in H-23 and 40% in H522 (FIG. 2).

Figure 3:
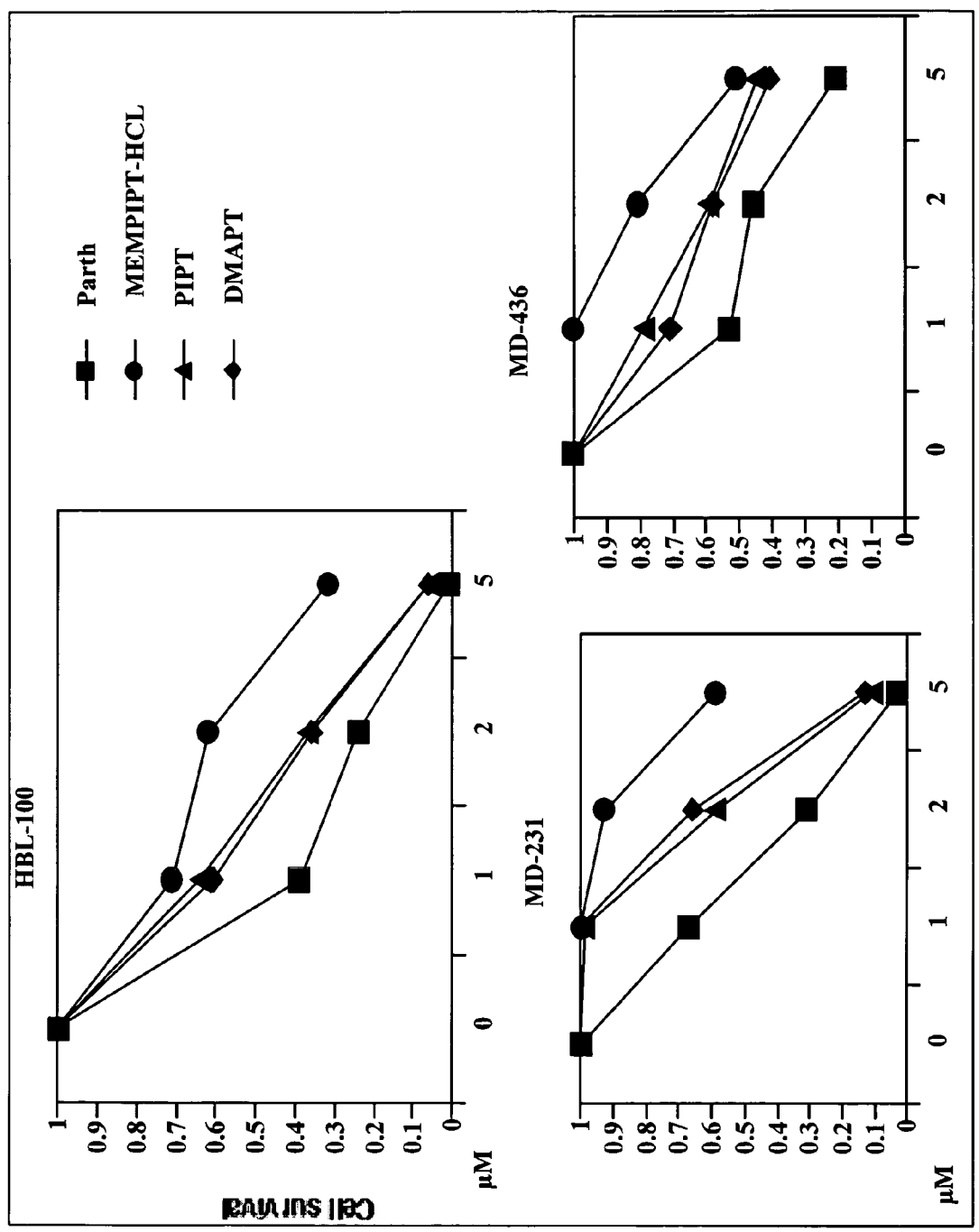
FIG. 3 shows the effectiveness of parthenolide and derivatives of the present invention in the MTS-PMS assay against breast cancer cell lines HBL-100, MD-231 and MD-436.

The breast cancer cell line clonogenic assay with hbl-100, mdl-231 and 436 cells showed almost complete inhibition of proliferation with DMAPT at 2 μm concentration. Similarly, parthenolide reduced proliferation with similar dosage ranges (FIG. 3).

We claim:
1. A compound of the formula:

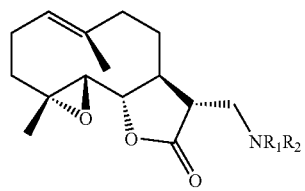

wherein:
$R_1$ is hydrogen, alkyl, substituted alkyl, hydroxyalkyl, alkenyl, substituted alkenyl, alkynyl, or substituted alkynyl; and $R_2$ is hydrogen, alkyl, substituted alkyl, hydroxyalkyl, alkenyl, substituted alkenyl, alkynyl, or substituted alkynyl; or $R_1$ and $R_2$ are together —$CH_2(CH_2)_nCH_2$— where n is 0 to 5; and together with N form an optionally substituted ring, said ring optionally fused to a cycloalkyl or aryl group to form a bicyclic or tricyclic system, said system optionally substituted and optionally comprising one or more heteroatoms; or $R_1$ and $R_2$ are together —$CH_2(CH_2)_nCH_2Z$-; where Z is O, S, Se, Si, P, —CO—, —SO—, —$SO_2$—, or —PO—; and n is 0 to 5; and together with N form an optionally substituted ring, said ring optionally fused to a cycloalkyl or aryl group to form a bicyclic or tricyclic ring system, said system optionally substituted and optionally comprising one or more heteroatoms; or $R_1$ and $R_2$ are together —$CH_2$-Z-$(CH)_b$—; where Z is O, S, Se, Si, P, —CO—, —SO—, —$SO_2$—, or —PO—; and a and b are independently 1 to 4; and together with N form an optionally substituted ring, said ring optionally fused to a cycloalkyl or aryl group to form a bicyclic or tricyclic ring system, said system optionally substituted and optionally comprising one or more heteroatoms; or a pharmaceutically acceptable salt thereof.

2. The compound of claim 1 wherein $R_1$ is hydrogen or optionally substituted lower alkyl; and $R_2$ is optionally substituted lower alkyl.

3. The compound of claim 2 wherein $R_1$ is methyl, ethyl, propyl or isobutyl.

4. The compound of claim 3 wherein $R_2$ is methyl or ethyl.

5. The compound of claim 1 wherein $R_1$ and $R_2$ are —$CH_2(CH_2)_nCH_2$— where n is 0 to 5; and together with N form an optionally substituted ring, said ring optionally fused to a cycloalkyl or aryl group to form a bicyclic or tricyclic system, said system optionally substituted and optionally comprising one or more heteroatoms.

6. The compound of claim 1 wherein $R_1$ and $R_2$ are —$CH_2(CH_2)_nCH_2Z$-; where Z is O, S, Se, Si, P, —CO—, —SO—, —$SO_2$—, or —PO—; and n is 0 to 5; and together with N form an optionally substituted ring, said ring optionally fused to a cycloalkyl or aryl group to form a bicyclic or tricyclic ring system, said system optionally substituted and optionally comprising one or more heteroatoms.

7. The compound of claim 1 wherein $R_1$ and $R_2$ are $-(CH_2)_a\text{-}Z\text{-}(CH_2)_b-$; where Z is O, S, Se, Si, P, $-CO-$, $-SO-$, $-SO_2-$, or $-PO-$; and a and b are independently 1 to 4; and together with N form an optionally substituted ring, said ring optionally fused to a cycloalkyl or aryl group to form a bicyclic or tricyclic ring system, said system optionally substituted and optionally comprising one or more heteroatoms.

8. The compound of claim 1 wherein $NR_1R_2$ form a ring selected from optionally substituted aziridin-1-yl, azetidin-1-yl, pyrrolidin-1-yl, piperidin-1-yl, homopiperidyn-1-yl and heptamethyleneimin-1-yl.

9. The compound of claim 1:
11βH, 13-Dimethylaminoparthenolide;
11βH, 13-Diethylaminoparthenolide;
11βH, 13-(tert-Butylamino)parthenolide;
11βH, 13-(Pyrrolidin-1-yl)parthenolide;
11βH, 13-(Piperidin-1-yl)parthenolide;
11βH, 13-(Morpholin-1-yl)parthenolide;
11βH, 13-(4-Methylpiperidin-1-yl)parthenolide;
11βH, 13-(4-Methylpiperazin-1-yl)parthenolide;
11βH, 13-(Homopiperidin-1-yl)parthenolide;
11βH, 13-(Heptamethyleneimin-1-yl)parthenolide;
11βH, 13-(Azetidin-1-yl)parthenolide; or
11βH, 13-Diallylaminoparthenolide.

10. The compound of claim 1:
11βH, 13-Dimethylaminoparthenolide hydrochloride;
11βH, 13-(Pyrrolidin-1-yl)parthenolide hydrochloride;
11βH, 13-(Piperidin-1-yl)parthenolide hydrochloride;
11βH, 13-(4-Methylpiperidin-1-yl)parthenolide hydrochloride;
11βH, 13-Dimethylaminoparthenolide maleate;
11βH, 13-Dimethylaminoparthenolide methiodide; or
11βH, 13-(4-Methylpiperidin-1-yl)parthenolide methiodide.

11. A pharmaceutical composition comprising a compound of claim 1 or a pharmaceutically acceptable salt thereof in combination with a pharmaceutically effective diluent or carrier.

12. A method of inhibiting cancer cell growth, comprising contacting said cells with an amount of a compound of claim 1 effective to inhibit the growth of said cancer cells.

13. The compound of claim 9: 11αH, 13-Dimethylaminoparthenolide.

14. The composition of claim 11 wherein the compound is 11αH, 13-Dimethylaminoparthenolide.

15. The method of claim 12 wherein the compound is 11αH, 13-Dimethylaminoparthenolide.

* * * * *

UNITED STATES PATENT AND TRADEMARK OFFICE
CERTIFICATE OF CORRECTION

PATENT NO. : 7,312,242 B2
APPLICATION NO. : 10/888274
DATED : December 25, 2007
INVENTOR(S) : Crooks et al.

It is certified that error appears in the above-identified patent and that said Letters Patent is hereby corrected as shown below:

In Claim 1, Column 24, line 43, the formula "$-CH_2-Z-(CH)_b-$" should be changed to:

$$-(CH_2)_a-Z-(CH_2)_b-$$

Signed and Sealed this

Seventh Day of September, 2010

David J. Kappos
*Director of the United States Patent and Trademark Office*